(12) United States Patent
Thompson

(10) Patent No.: US 6,453,195 B1
(45) Date of Patent: Sep. 17, 2002

(54) CLOSED LOOP DRUG DELIVERY SYSTEM AND REMOTE MANAGEMENT THEREOF

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/811,685

(22) Filed: Mar. 19, 2001

(51) Int. Cl.$^7$ ............................................... A61N 1/362
(52) U.S. Cl. ............................................................ 607/3
(58) Field of Search ............................... 604/20; 607/3, 607/4, 5, 9, 13

(56) References Cited

U.S. PATENT DOCUMENTS

| | | |
|---|---|---|
| 5,087,243 A | 2/1992 | Avitall |
| 5,135,480 A | 8/1992 | Bannon et al. |
| 5,292,338 A | 3/1994 | Bardy |
| 5,314,430 A | 5/1994 | Bardy |
| 5,345,362 A | 9/1994 | Winkler |
| 5,527,344 A | 6/1996 | Arzbaecher |
| 5,549,642 A | 8/1996 | Min et al. |
| 5,662,689 A | 9/1997 | Elsberry et al. |
| D384,745 S | 10/1997 | Lattin et al. |
| 5,683,432 A | 11/1997 | Goedeke et al. |
| 5,733,259 A | 3/1998 | Valcke et al. |
| 5,817,131 A | 10/1998 | Elsberry et al. |
| 5,836,989 A | 11/1998 | Shelton |
| 5,843,139 A | 12/1998 | Goedeke et al. |
| 5,893,881 A | 4/1999 | Elsberry et al. |
| 5,925,066 A | 7/1999 | Kroll et al. |
| 5,995,869 A | 11/1999 | Cormier et al. |
| 6,035,234 A | 3/2000 | Riddle et al. |
| 6,086,572 A | 7/2000 | Johnson et al. |
| 6,091,989 A | 7/2000 | Swerdlow et al. |

FOREIGN PATENT DOCUMENTS

WO 9218198 10/1992 ............ A61N/1/39

OTHER PUBLICATIONS

Arzbaecher, Robert et al., *PACE*, "Automatic Tachycardia Recognition," vol. 7, May–Jun. 1984, Part II, p. 541–7.
Blanc, J.J. et al., *Cardiac Pacing*, "Safety and feasibility of transvenous cardioversion in atrial tachycardia," 1985, p. 1526–9.

*Primary Examiner*—Scott M. Getzow
(74) *Attorney, Agent, or Firm*—Girma Wolde-Michael

(57) ABSTRACT

A transdermal drug delivery device in communication with at least one IMD is externally mounted to deliver pain analgesics and/or threshold reduction medications prior to or contemporaneous with a shock associated with a pacer, a defibrillator and similar therapy device. The drug delivery device includes an attachable strip with a storage for medications and is epidermally mounted. The medications are released into the bloodstream in response to an indication that the IMD is about to deliver a shock. The drug delivery device is adapted for use with various drugs. Further, the delivery of drugs could be controlled by the patient to provide a semi-automatic use and/or to terminate delay shock. The transdermal drug delivery device and the IMD include system status indicators to provide real-time operational data of the drug delivery device and the IMD individually and in combination. The drug delivery device is also implemented with a CHF monitor to treat CHF patients.

46 Claims, 7 Drawing Sheets

CLOSED LOOP DRUG DELIVERY SYSTEM AND REMOTE MANAGEMENT THEREOF

FIELD OF THE INVENTION

The present invention generally relates to medical devices. Specifically, the invention relates to communication between an implanted medical device and an external drug delivery device in wireless data communication thereof. More specifically, the invention relates to a system that automatically delivers analgesic and/or threshold reduction medications prior to the application of cardiac shock or drug delivery for pulmonary hypertension, for example, using RV pressure. The release of the drug is coordinated between the implanted device and the external device via the wireless communication system. The invention also provides remote management of a patient wherein drug delivery data from the external device and therapy information from the implanted device are transferred to a remote location using various methods of data transfer to enable physicians and caregivers to remotely review and monitor the patient as needed. In one aspect of the present invention, the drug delivery dose and frequency of treatment are preferably controlled via parametric modifications and adjustments of the implanted medical device. In yet another embodiment, the external drug delivery device is directly programmed overriding communication signals that initiate and call for drug delivery from the implanted medical device.

BACKGROUND OF THE INVENTION

Current practice of implanting both a therapeutic medical device such as a cardiac pacemaker, defibrillator, etc., in conjunction with implantable drug pumps is cumbersome and expensive to manage. Further, for example, with a defibrillator and an implanted drug delivery device, one would need to run a catheter to deliver the drug in addition to leads for the defibrillator. Most implanted drug delivery devices known in the art, do not deliver drugs directly into the bloodstream.

The alleviation of cardioversion shock pain has been the subject of various patents in the prior art. Most of the pain-alleviating therapy, in conjunction with the delivery of cardioversion energy to the heart chamber is well known in the art. Further, the alleviation of pain through the operation of implantable drug dispensers for automatically, periodically, delivering a bolus of a pain-alleviating drug at the site in the body are also well known in the art. For example, U.S. Pat. Nos. 5,662,689 and 5,817,131 to Elsberry et al, disclose a methods and apparatus for alleviating cardioversion shock pain. The disclosures include an implantable cardioverter for providing cardioversion electrical energy to at least one chamber of a patient's heart in need of cardioversion and applying a pain alleviating therapy at an appropriate site in the patient's body prior to, or in conjunction with, the delivery of the cardioversion energy to the heart chamber to alleviate propagated pain perceived by the patient. The combined cardioversion and pain alleviating therapies are preferably realized in a single implantable, multi-programmable medical device or separate implantable cardioversion and pain control devices with means for communicating operating and status commands between the devices through the patient's body.

U.S. Pat. No. 5,893,881 issued to Elsberry et al discloses a method and apparatus for alleviating cardioversion shock pain by delivering a bolus of analgesic. Specifically, the invention discloses an implantable cardioverter for providing cardioversion electrical energy to at least one chamber of a patient's heart in need of cardioversion and applying a pain alleviating therapy at an appropriate site in the patient's body prior to or in conjunction with the delivery of the cardioversion energy to the heart chamber to alleviate propagated pain perceived by the patient. The combined cardioversion and pain alleviating therapies are preferably realized in a single implantable, multi-programmable medical device or separate implantable cardioversion and pain control devices with means for communicating operating and status commands between the devices through the patient's body.

U.S. Pat. No. 5,087,243 to Avitall discloses a myocardial iontophoresis device. An implantable iontophoretic delivery system for use in applying medicinal materials rapidly to specific subcutaneous tissue sites of interest in conjunction with an implanted defibrillator is disclosed which uses a subcutaneously situated pouch for supplying medication in conjunction with a pair of defibrillator electrodes connected to a power source. One of the electrodes is located proximately with respect to the tissue of interest and is designed to dispense the medication of interest utilizing controlled electrical pulses. The pouch is connected with the administering electrode of the electrode system via pumping mechanism.

U.S. Pat. No. 5,733,259 to Valcke et al discloses a method and apparatus for closed loop drug delivery. Specifically, a closed-loop drug delivery system uses patient response and rule based decision-making methods to achieve operator specified responses for diagnostic purposes. In the preferred embodiment, cardiac diagnosis is performed by pharmacologically stressing the heart by administration of an exercise simulating agent drug. In the preferred method, a protocol is defined, which preferably includes a target for a physiologic variable, such as heart rate, and a plan to achieve that target value. Preferably, the plan includes a specification of the desired rate of increase in that variable, such as the rate of increase in the heart rate per minute. The plan comprises the desired changes in the physiologic variable as a function of time.

U.S. Pat. No. 5,925,066 to Kroll et al discloses an atrial arrhythmia sensor with drug and electrical therapy control apparatus. The invention relates to an atrial arrhythmia sensor and drug-dispensing apparatus is disclosed. The apparatus comprises a multiphase, multistage intelligent system to monitor and treat atrial fibrillation. The apparatus includes atrial rate sensing means, cardiac pacing and anti-tachycardia pacing means, drug delivery means including a self-cleaning catheter line with multi-drug dispensing capability preferably operated using a dual pump arrangement and an iontophoretic device. The drug delivery system may also include a porous catheter to discharge drug into the atrium. The intelligent system includes a memory implemented logic (software) to continuously monitor the atrial rate and initiate a response of either cardiac pacing, anti-tachycardia pacing or drug dispensing based on preset cardiac activity parameters. The system also includes a medical history-recording feature.

U.S. Pat. No. 5,527,344 to Arzbaecher et al discloses a pharmacological atrial defibrillator and method. In this invention, a method and an implantable apparatus for automatically delivering a defibrillating drug to a patient upon detection of the onset of atrial fibrillation are disclosed. Atrial activity of a heart is detected and monitored. A delivery time is continuously computed and a delivery signal is emitted as a function of the monitored level of the atrial activity. When the delivery signal is emitted, an infusion pump discharges a defibrillating drug into the bloodstream of the patient. The atrial activity is also continuously monitored for computing a pacing time at which a pacing signal is emitted as a second function of the monitored level of atrial activity. When the pacing signal is emitted a pacer paces the atrium of the heart.

U.S. Pat. No. 5,135,480 to Bannon et al discloses a transdermal drug delivery device. More specifically, the invention relates to a transdermal device having a detachably mounted electrode with a first surface adapted for contact with human skin and through which a drug substance contained in the electrode passes to the skin under the influence of an iontophoretic or electro-osmotic force and a second surface which is electrically conducting, the electrode has a surface area in contact with the skin, in use, in the range 0.1 to 30 cm and a drug dissolved or dispersed in a hydrophilic medium at a concentration in the range 0.1 to 15% (w/v) based on the hydrophilic medium.

U.S. Pat. No. 6,091,989 to Swerdlow et al discloses a method and apparatus for reduction of pain from electric shock therapies. The invention discloses a method and apparatus for pretreating a patient prior to a therapeutic painful stimulus, comprising the application of pain inhibiting stimuli to a patient prior to an application of the therapeutic painful stimulus. Applying pain-inhibiting stimuli comprises the steps of sensing a need for the therapeutic painful stimulus, preparing to deliver the pain inhibiting stimuli to the patient prior to applying the therapeutic painful stimulus, and delivering the pain inhibiting stimuli to the patient prior to applying the therapeutic painful stimulus. The method and apparatus are embodied in a fully automatic; fully implantable, single or dual chamber atrial or ventricular cardioverter-defibrillators. The pain inhibiting prepulse method is intended primarily for use in conscious patients but may also be used in sleeping patients.

As can be seen from the prior art recited hereinabove, alleviation of cardioversion shock pain is an important consideration in cardiac therapy. However, there is a need for a closed loop controlled system to automatically deliver pain analgesics and/or threshold reduction medications prior to or contemporaneous with an atrial defibrillation shock or other drug delivery therapy that may be associated with discomfort or pain.

SUMMARY OF THE INVENTION

The present invention generally relates to a drug delivery device in wireless communication with an implanted medical device that preferably provides drugs transdermally prior to the delivery of therapy by the implanted device. The system is preferably telemetry or wireless communication-enabled to exchange data with the implanted device to thereby identify preshock events so that shock attenuation drugs could be delivered prior to an atrial defibrillation shock. More specifically, an iontophoretic drug delivery device is externally mounted on a patient's body, and is interconnected by communication transmission channel with an implanted medical device in the patient. The external device and the implanted medical device are in a bi-directional data exchange using telemetry and equivalent wireless communication systems therebetween.

Further, the external iontophoretic drug delivery device and the implanted medical device are independently accessible to a programmer or an Independent Remote Monitor (IRM) external device for interrogation and reprogramming of parameters as needed. Furthermore, through either the IRM or a programmer, data may be transmitted to a PC for review by physicians or caregivers. Similarly, the data may be transferred to a server, which may be accessible to a plurality of users of the data for analysis, follow-up or research and development purposes.

Further, through media such as the Internet, intranet, extranet or World Wide Web, data from the server may be accessible by third parties, remotely to follow-up the patient and provide recommendations for adjustment or therapy as needed.

One aspect of the invention relates to the provision of one or more therapy regimens to the body, including two or more discreet medical devices, at least one of which medical devices is implanted into the living body and the other externally mounted, and being in bi-directional data communication and exchange with the implanted device.

Yet another aspect of the invention includes monitoring a condition of a living body on a continuous basis to provide a shock attenuation therapy before cardioversion electrical energy is applied to at least one chamber of a patient's heart. Continuous monitoring and communication between the external device and the internal device coordinates the delivery of drug from the external device before shock is delivered by the implanted medical device. In this aspect of the invention, the external device and the internal device communicate and identify preshock conditions that indicate the imminence of cardioversion.

Yet another aspect of the invention includes a remote communication system in which an external drug delivery device is monitored and actuated to respond to indications of events that would trigger therapy by an implanted medical device, which may result in the perception of pain by the patient. The external device may be remotely programmed to deliver drugs transdermally immediately before or contemporaneous with the therapy. Similarly, the communication system would allow a remote review and programming of the implanted device. Further, amounts of pain reducing drugs to be delivered may be remotely adjusted to complement changes in cardioversion therapy.

DETAILED DESCRIPTION OF THE PREFERRED EMBODIMENT

Figure 1:
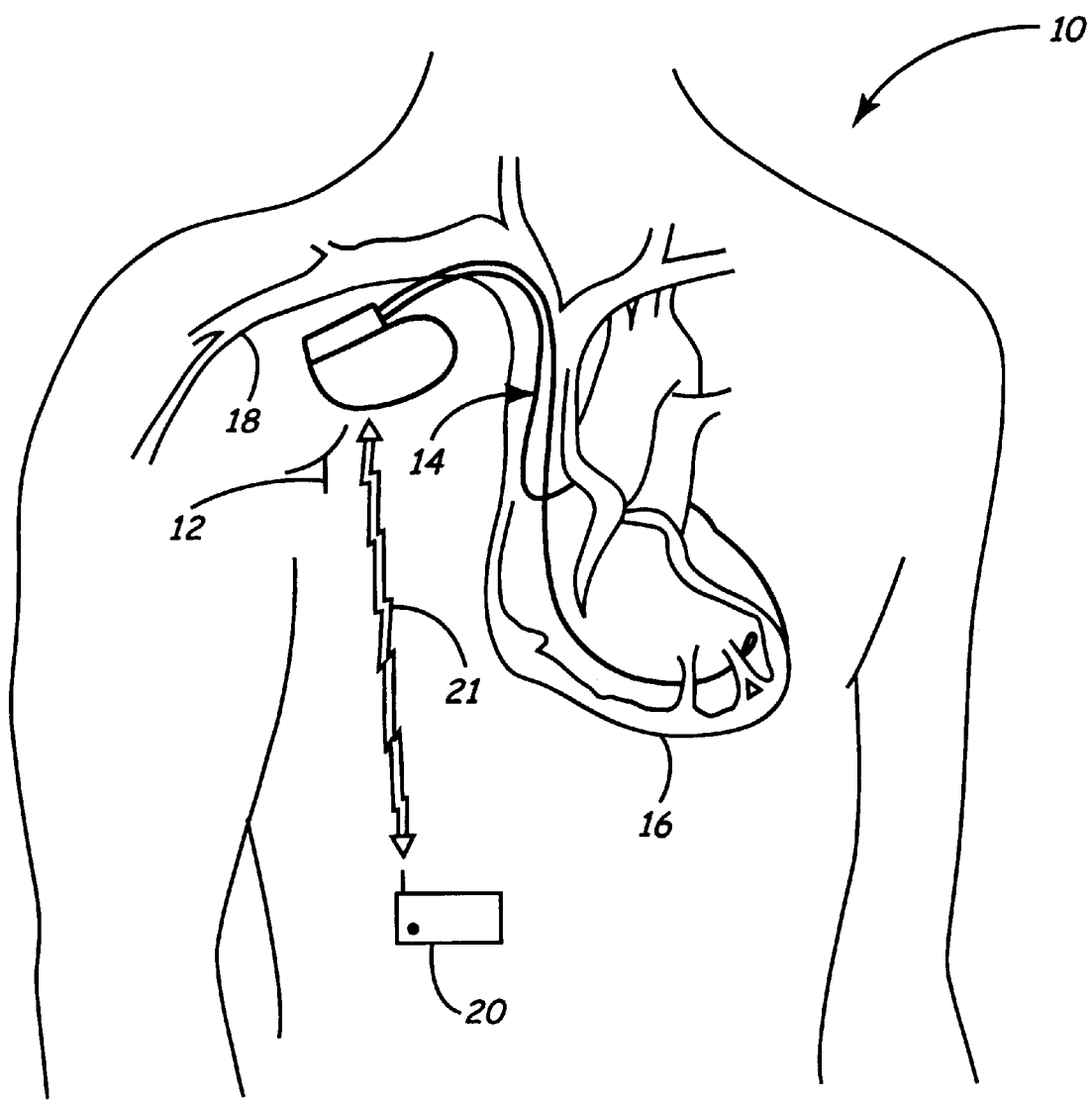
FIG. 1 represents externally mounted drug delivery in bi-directional communications with an implanted medical device.

FIG. 1 is an illustration of an implantable medical device, for instance, IMD adapted for use to communicate with an externally mounted drug delivery device. The IMD implanted in patient 10 includes IMD 12. In accordance with conventional practice in the art, IMD 12 is housed within a hermetically sealed biologically inert outer casing which may itself be conductive so as to serve as an indifferent electrode in the IMD's pacing cardioversion/sensing circuit. One or more pacemaker leads collectively identified with reference number 14 are electrically coupled to IMD 10 in a conventional manner and extend into the patient's heart 16 via vein 18. Disposed generally near the distal end of leads 14 are one or more exposed conductive electrodes for receiving electrical cardiac signals and/or for delivering electrical pacing and/or cardioversion/defibrillation stimuli to heart 16. As will be appreciated by those of ordinary skill in the art, leads 14 may be implanted with its distal end situated in the atrium and/or ventricle of heart 16.

Although the present invention will be described herein in one embodiment, which includes an implanted medical device, those of ordinary skill in the art having the benefit of the present disclosure will appreciate that the present invention may be practiced in connection with numerous other types of implantable medical device systems. As to every element, it may be replaced by any one of infinite equivalent alternatives, only some of which are disclosed in this specification.

As depicted in FIG. 1, external drug delivery device 20 is linked via telemetry transmission 21 to IMD 12.

Figure 2:
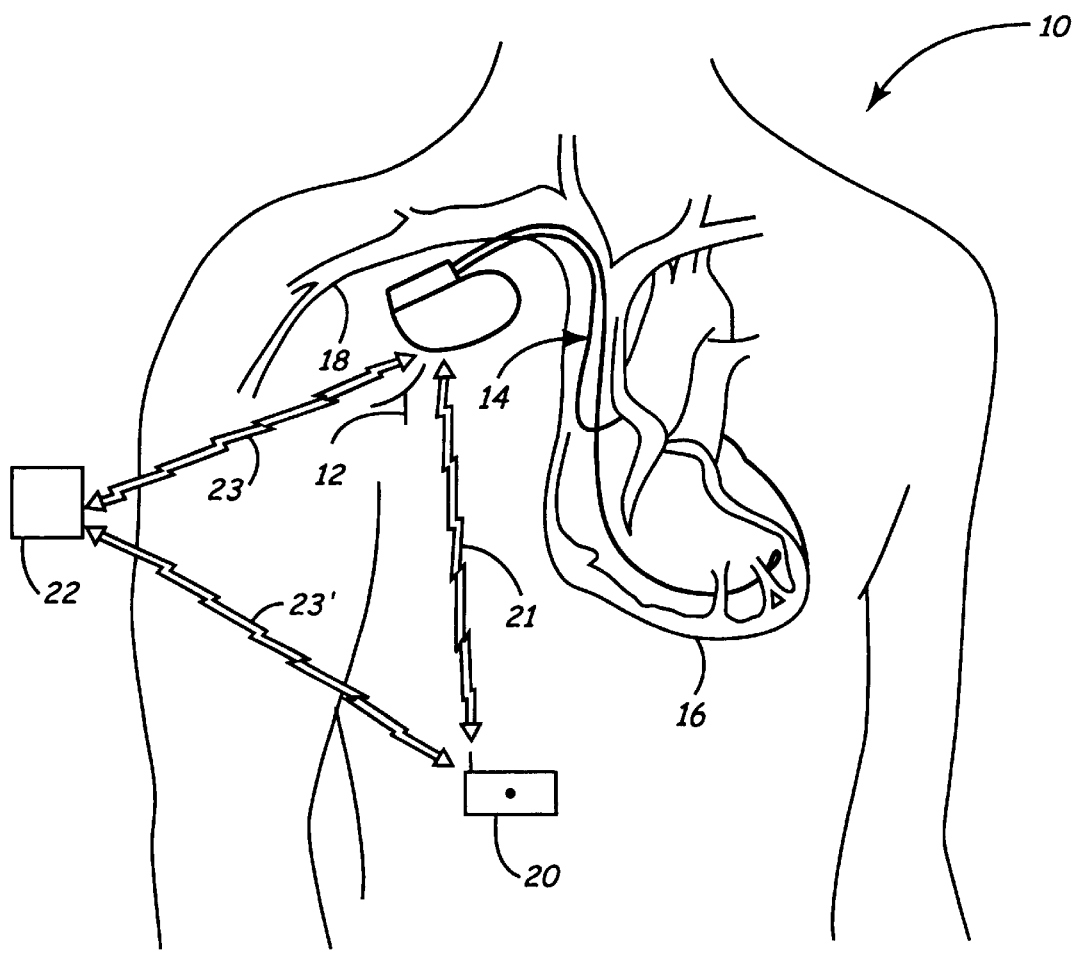
FIG. 2 shows an external programmer or a remote home device such as used to uplink and downlink data with both external drug delivery device and the implanted medical device.

FIG. 2 is a variation of FOG. 1 in which programmer 22 is shown in communication with implanted medical device 12 and external drug delivery system 20. Specifically, programming unit 22 is in telemetry or wireless communication with implanted medical device 12 and external drug delivery device 20 via uplink and downlink communication channels 23 and 23', respectively. Programmer 22 described herein with reference to FIG. 2 is disclosed in more detail in U.S. Pat. No. 5,345,362 issued to Thomas J. Winkler entitled "Portable Computer Apparatus with Articulating Display Panel" which patent is hereby incorporated herein by reference in its entirety. Similarly, other remote devices that enable programming of IMD 12 and drug delivery device 20 such as a home monitor disclosed in U.S. Pat. applications Ser. No. 09/776,265 and 60/190,272 entitled "Information Remote Monitor (IRM) Medical Device" and "Heart Failure Quick Look Summary for Patient Management Systems" respectively, which are hereby incorporated herein by reference in their entireties.

Figure 3:
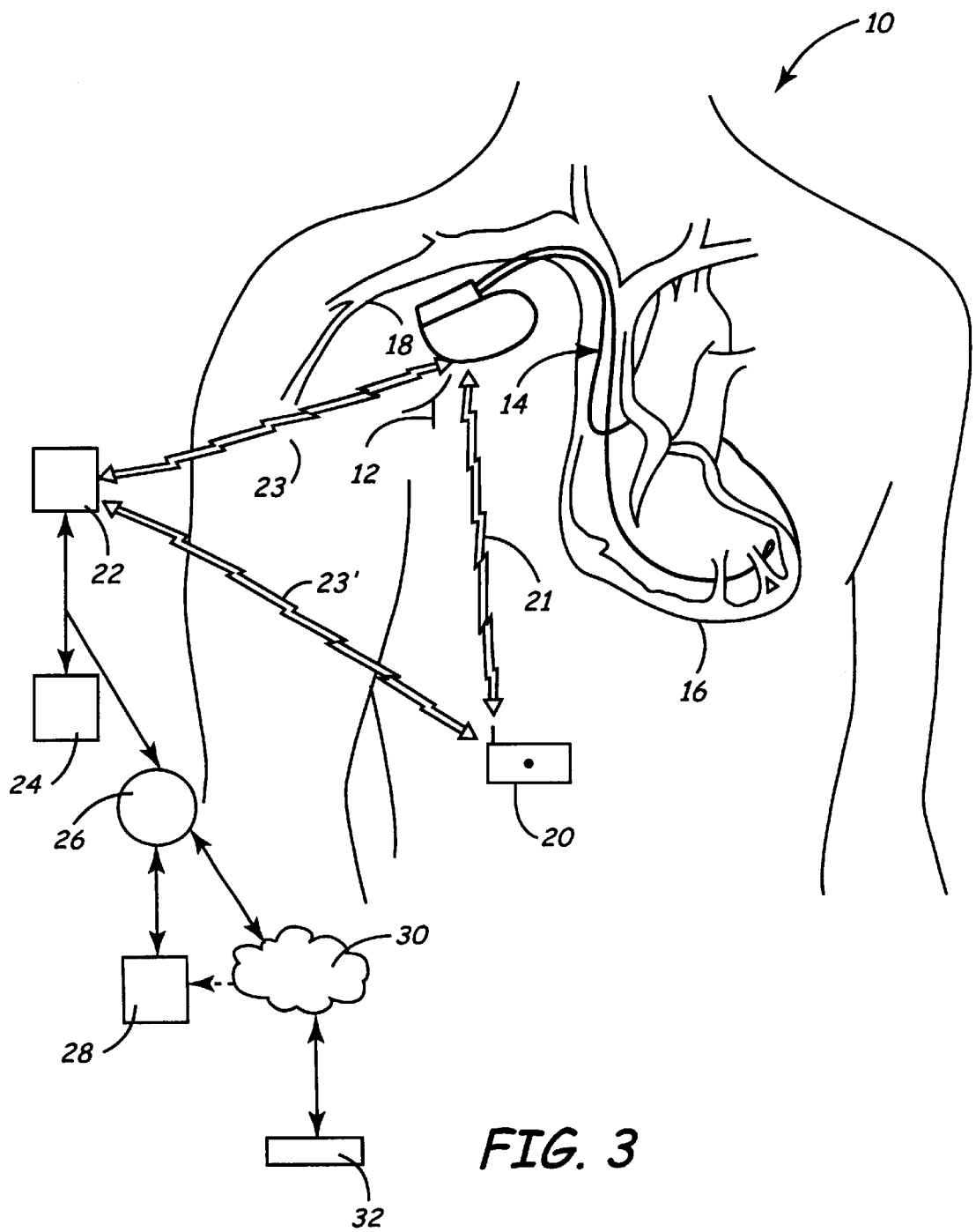
FIG. 3 represents one aspect of the remote communication and monitoring system of the present invention.

FIG. 3 is another embodiment of the present invention wherein data is communicated using various medium to transfer information from IMD 12 and drug delivery device 20 via programmer, IRM or equivalent device 22. As discussed hereinabove data from IMD 12 and drug delivery device 20 is uplinked to device 22 from which it may be directed to a PC 24 or server 26 using, for example, a modem, an ISDN line, fiber optic, cable, infrared, bluetooth-enabled or equivalent direct or wireless communication systems. Server 26 is also accessible directly to qualified users at station 28. Further, server 26 may be accessible via Internet 30 to remote users 32.

With this exemplary communication network, caregivers, physicians and other qualified personnel may be able to access and review or reprogram the operations of IMD 12 and drug delivery device 20 remotely. For example, user 28 may use a LAN1 or other secure lines to access server 26 from which either current or stored data relating to the operation of IMD 12 and drug delivery device 20 could be obtained for evaluation and adjustment, or remote patient monitoring. Similarly, remote users at station 32 may be able to access operational and functional data of IMD 12 and drug delivery device 20 via Internet 30.

One of the significant aspects of the present invention is the use of a transdermally operable drug delivery device 20. It is similar to the electrotransport drug delivery system disclosed in Design Pat. No. 384,745 to Lattin et al. Further, a similar device is disclosed in U.S. Pat. No. 5,995,869 to Cormier et al. Additionally, electrotransport delivery device with voltage boosting circuit is disclosed in U.S. Pat. No. 6,035,234 to Riddle et al. And an electrotransport device and method of setting the output using the same drug delivery device is disclosed in U.S. Pat. No. 6,086,572 to Johnson et al. which patent applications are incorporated herein by reference in their entireties.

The present invention implements a highly adaptable communication link between the implanted device and the drug delivery device disclosed in the prior art. The communication system, as indicated hereinabove without limitation could be telemetry or as substantially described in U.S. Pat. No. 5,683,432 and 5,843,139, or an equivalent medical device communication system such as the one disclosed in U.S. Pat. No. 4,987,897 to Funke which patent is herein incorporated by reference in its entirety. Accordingly, the present invention provides a closed-loop drug delivery system that operates in data communications with an implanted device to attenuate the impact of shock and other discomfort resulting from IMD therapy.

Figure 4:
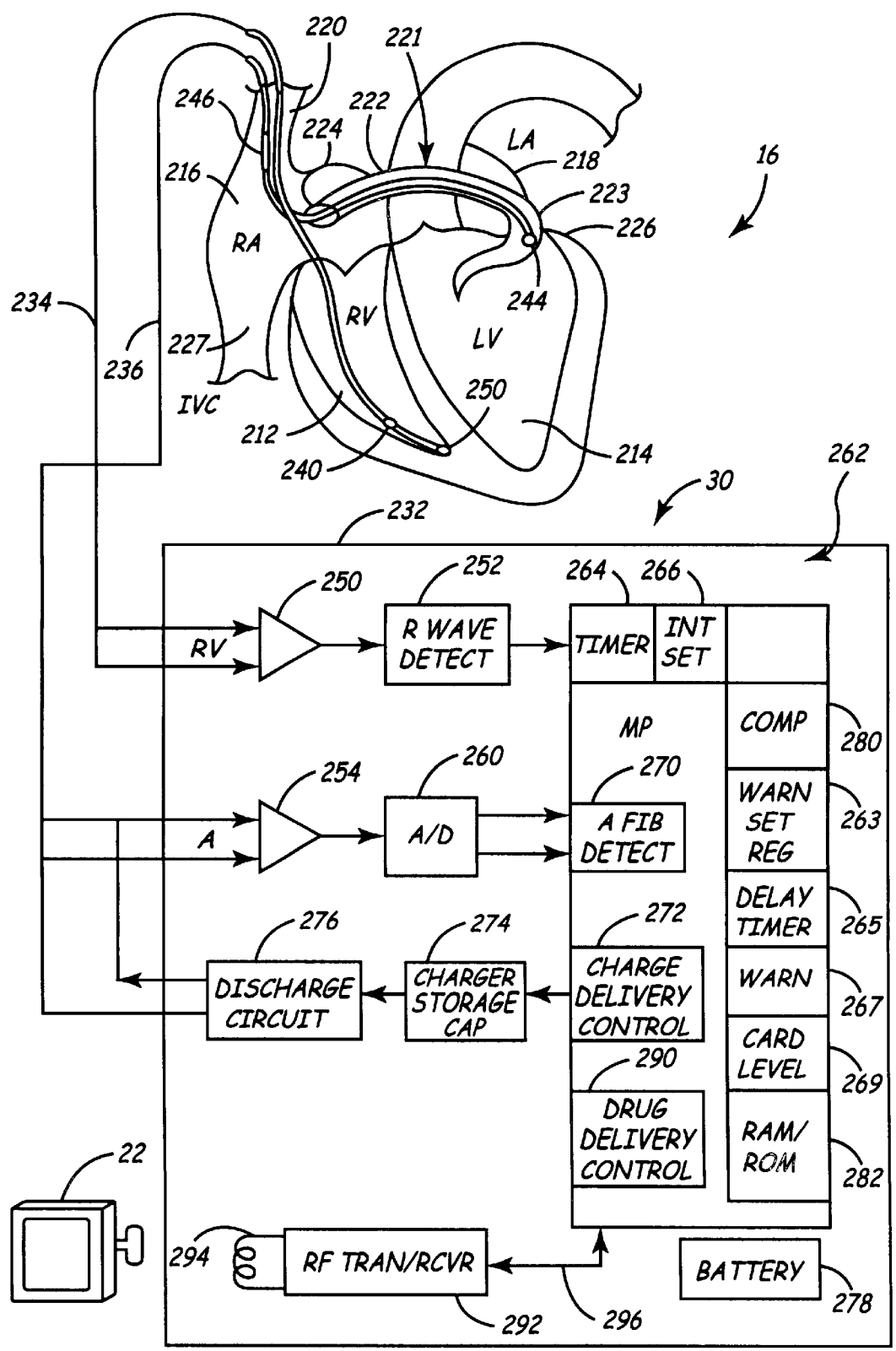
FIG. 4 is a schematic block diagram of an automatic atrial cardioverter and pain alleviating system of the present invention employing the automatic remote delivery of pain alleviating drug therapy.

Referring now to FIG. 4, a fully implantable atrial cardioverter system 12 embodying the present invention in association with a schematically illustrated human heart 16 in need of atrial fibrillation monitoring and potential cardioversion of the atria 216, 218 and an external programmer 22 are shown. The atrial cardioverter system 12 is capable of the sequential initiation of delivery of a pain alleviating analgesic at therapeutic levels followed by delivery of atrial cardioversion electrical energy pulses or shocks of sufficient amplitude and duration to effectively cardiovert the heart 16 in atrial fibrillation. The portions of the heart 16 illustrated in FIG. 4 are the right ventricle (RV) 212, the left ventricle 214, the right atrium (RA) 216, the left atrium 218, the SVC 220, the CS 221 including the CS ostium or opening 224, the left ventricular free wall 226 and the inferior vena cava 227.

The system 30 generally includes an enclosure 232, for hermetically sealing the internal circuit elements, battery, telemetry antenna, a bipolar RV lead 234, and a RA-CS lead 236. The enclosure 232 and leads 234 and 236 are arranged to be implanted beneath the skin of a patient so as to render the atrial cardioverter system 30 fully implantable.

The RV lead 234 preferably comprises an endocardial bipolar lead having electrodes 238 and 240 arranged for establishing electrical contact with the right ventricle 212 of the heart 16. The electrodes 238 and 240 permit bipolar sensing of ventricular depolarizations or R-waves in the right ventricle 212. As illustrated, the lead 234 is preferably fed through the SVC 220, the right atrium 216, and then into the right ventricle 212 to lodge the electrodes 238, 240 in the apex thereof as illustrated.

The RA-CS lead 236 generally includes a tip or CS cardioverting electrode 244 and a proximal ring or RA cardioverting electrode 246 as shown in U.S. Pat. No. 5,165,403, for example. As illustrated, the RA-CS lead 236 is flexible and arranged to be passed down the superior vena cava 220, into the right atrium 216, into the coronary sinus ostium 224. The CS electrode 244 is advanced into the coronary sinus channel 221 of the heart near the left side thereof so that the first or tip electrode 244 is within the coronary sinus channel 221 either within the coronary sinus 222 adjacent the left, ventricle 214 and beneath the left atrium 218 or most preferably within the great cardiac vein 223 adjacent the left ventricle 214 and beneath the left atrium 218. The electrodes 244 and 246 are spaced apart such that when the CS electrode 244 is positioned as described above, the RA electrode 246 is in the right atrium 216. The CS electrode 244 together with the RA electrode 246 provides bipolar sensing of heart activity in the atria 216 and 218.

The CS electrode 244 and the RA electrode 246 also provide for the delivery of defibrillating electrical energy to the atria. Because the CS electrode 244 is located beneath the left atrium 218 near the left ventricle 214 and the RA electrode 246 is within the right atrium 216, the cardioverting electrical energy, when applied between these electrodes will be substantially confined to the atria 216 and 218 of the heart 16. As a result, the electrical energy applied to the right ventricle 212 and left ventricle 214 when the atria are cardioverted or defibrillated will be minimized. This greatly reduces the potential for ventricular fibrillation of the heart to be induced as a result of the application of cardioversion electrical energy of the atria of the heart.

Further electrode systems and cardioversion pathways have been disclosed and are suitable for use in the practice of the present invention. One such atrial cardioversion electrode system is disclosed in the article "Safety and Feasibility of Transvenous Cardioversion in Atrial Tachycardia", by Blanc et al., published in Cardiac Pacing, edited by Gomez, Future Pub. Co., 1985, pp 1526–1529. This electrode system employs a single lead with electrodes located in the right atrium and in the pulmonary artery. Delivery of atrial cardioversion shocks between an RV electrode and a subcutaneous electrode is disclosed in U.S. Pat. No. 5,292,338. Delivery of atrial defibrillation pulses between a coronary sinus electrode and a subcutaneous electrode is also disclosed in U.S. Pat. No. 5,314,430.

A further suitable atrial cardioversion electrode system is disclosed in U.S. Pat. No. 5,549,642 incorporated herein by reference in its entirety. The electrode system disclosed therein includes an RA/SVC electrode (alone or optionally coupled to a subcutaneous electrode) and a CS electrode. The elongated RA/SVC electrode appears to provide atrial defibrillation thresholds in the range of about 1.0 Joule or less across a substantial portion of the patient population which represents a substantial improvement over the RA or SVC to CS/great vein electrode system employed in the above-referenced '403 patent.

Any of the above atrial cardioversion electrode systems and associated atrial and/or ventricular leads may be used in the practice of the present invention. However, even an approximately 1.0 joule cardioversion shock can be painful to a substantial portion of the population, particularly since atrial fibrillation episodes repeat frequently, requiring frequent cardioversion.

Within the enclosure 232, the system 30 includes a ventricular sense amplifier 250 coupled to the RV lead 234 to receive electrical signals in the ventricle across the bipolar electrode pair 238, 240 and an R-wave detector 252 to detect the R-waves therefrom. The ventricular sense amplifier 250 and the R-wave detector 252 form a first detecting means that senses R-waves in the electrogram transmitted to ventricular sense amplifier by the RV lead 234. The R-wave detector 252 is of the type well known in the art, which provides an output pulse upon the occurrence of an R-wave being sensed during a cardiac cycle of the heart. The delivery of the atrial defibrillation shock or pulse is timed from the R-wave employing the ventricular timer 264 as described below.

The lead and electrode systems in certain embodiments of the above-referenced '338, '403 and '430 and '642 patents include an RV defibrillation electrode positioned on an RV lead inserted into the right ventricle and a pair of ventricular sense electrodes. Alternatively, in the atrial cardioversion system depicted in FIG. 4, common ventricular pacing leads having bipolar screw-in ventricular electrodes of this type may be employed as pace/sense electrodes 238, 240.

An atrial sense amplifier 254 is coupled to the RA-CS lead 236 to receive electrical signals or P-waves across the right atrium 216. The atrial sense amplifier 254 forms a second detecting means for detecting P-wave atrial activity of the heart picked up by the CS electrode 244 and RA electrode 246 of the RA-CS lead 236. The P-wave output signal of the atrial sense amplifier 254 is coupled to an analog to digital converter 260 which converts the analog signal representative of the atrial activity of the heart to digital samples for further processing to determine if atrial fibrillation is present and if the atrial cardioversion shock is effective in converting the atria to a normal atrial rate.

The enclosure 232 of the atrial cardioverter system 30 further include a microcomputer 262 that is preferably implemented in a manner disclosed in the above-referenced '338 patent and further as described hereinafter with respect to the flow diagram of FIG. 7. The implementation of the microcomputer 262 in accordance with this embodiment of the present invention results in a plurality of functional stages and RAM/ROM 282 for storing operating algorithms and programmable parameters as well as accumulated operating data for subsequent telemetry out to the external programmer 22.

The circuitry includes the ventricular timer 264 for timing various intervals that recur in each QRST cycle as well as the R-wave synchronization time interval, an interval set stage 266 for selecting time intervals to be timed out in the ventricular timer 264, a delay timer 265 for timing out further delay times set in interval set stage 266 for the delivery of the pain alleviating therapy, an optional patient warning device 267 and warning set register 263, a cardioversion energy level set stage 269, an atrial fibrillation detector 270, a charge delivery control stage 272, an analgesic delivery control stage 290, and a computation stage 280.

The microcomputer 262 is arranged to operate in conjunction with RAM/ROM memory 282 which may be coupled to the microcomputer 262 by a multi-bit address bus and a bi-directional multiple-bit data bus. This permits the microcomputer 262 to address desired memory locations within the memory for executing write or read operations. During a write operation, the microcomputer 262 stores data, such as time intervals or operating parameters in the memory 282 at the addresses defined by multiple-bit data bus. During a read operation, the microcomputer 262 obtains data from the memory at the storage locations identified by the multiple-bit addresses provided over the address bus and receives the data from the memory 282 over the bi-directional data bus. Data related to the detections of atrial fibrillation and the deliveries of the therapies may be recorded in the RAM memory 282 for interrogation and telemetry out to the external programmer 22 in a manner well known in the art.

Detection of atrial fibrillation may be accomplished in atrial fibrillation detector 270, in conjunction with computation stage 280, of microcomputer 262 from the digitized P-waves detected by atrial sense amplifier 254 using any of the various atrial fibrillation detection methodologies known to the art. Generally, atrial fibrillation may be detected in response to an extended series of high rate (e.g. 240 BPM or greater) atrial depolarizations or P-waves. If greater specificity for atrial fibrillation is desired, analysis of regularity of rate waveform morphology may also be employed.

Termination of atrial fibrillation may be detected in response to a decrease in the rate of atrial depolarizations and/or an increase in their regularity.

Appropriate detection methodologies are disclosed in the article "Automatic Tachycardia Recognition", by Arzbaecher et al., published in PACE, Vol. 7, May-June 1984, part II, pages 541–547 and in PCT Application No. US92/02829, Publication No. WO 92/18198 by Adams et al., both incorporated herein by reference in their entireties. In the PCT application, careful synchronization of the high voltage atrial defibrillation pulse to the ventricles to avoid induction of ventricular tachycardia or fibrillation is also discussed.

In addition, in the context of devices which automatically detect the occurrence of atrial fibrillation, the patient may optionally be warned of the detection of atrial fibrillation to be ready for the delivery of the atrial cardioversion shock through operation of the warning device 267. In this alternate variation of the embodiment of the invention, a warning may be provided to the patient of the diagnosis of atrial fibrillation and the commencement of delivery of the pain alleviation drug therapy. The warning may be effected in the manner described in U.S. Pat. No. 5,332,400 incorporated herein by reference in its entirety, but is preferably effected by energizing a piezoelectric crystal oscillator that oscillates at an audible frequency intense enough for the patient to hear it and take precautions, if necessary. The patient may also optionally be provided with a limited function programmer 22 for use in communicating a command to the microcomputer 262 to prevent delivery of the cardioversion shock until the patient feels the effects of the pain alleviation therapy, at which time the patient may employ the programmer 22 to enable delivery of the cardioversion shock, subject to re-verification of the presence of the atrial fibrillation.

In this regard, the system 30 also includes the warning set register 263, the delay timer 265, and the warning device 267 that are utilized for generating the warning alarm for the patient when the atrial fibrillation detector 270 determines that the atria are in fibrillation. The warning device 267 may constitute an audible alarm sounding piezoelectric crystal oscillator for warning the patient that atrial fibrillation has been detected and that cardioverting electrical energy will be applied to the patient's atria.

If a programmer 22 is provided, it may also optionally include a patient activated command signal to initiate the delivery of the pain alleviating and cardioversion therapies in response to symptomatic atrial fibrillation. In this context as well, the ability to use the programmer 22 to delay the delivery of the cardioversion pulse until the patient has felt the effects of the pain alleviating therapy is believed valuable.

After the fibrillation detection warning is delivered to the patient, or after the patient requests cardioversion therapy by means of the programmer 22, register 263 is set to indicate that the patient has received the fibrillation detection warning or has requested therapy. Immediately thereafter, the delay timer 265 starts timing the warning delay period and initiates communication to drug delivery system 20 via RF transmitter 292 and antenna 294. The delay period defines a time interval from when the patient receives the warning or requests therapy to when the patient should first expect to receive the cardioverting electrical energy. The delay time is preferably programmable between one minute and twenty minutes to afford sufficient time to permit the pain alleviating therapy to take effect and for the patient to prepare for receiving the atrial cardioverting electrical energy. A second warning may optionally be given slightly before delivery of the cardioversion pulse, if desired. If the patient does not perceive the analgesic effect of the pain alleviating therapy during the warning delay, the patient may use the programmer 22 to reset the delay timer 265 to delay delivery of the cardioversion pulse until timer 265 expires. Alternatively, the programmer may instead allow the patient to delay delivery of the pulse until the patient perceives the analgesic effect, and allow delivery of the cardioversion therapy only following a patient initiated enable signal to the implanted device indicating that therapy may be delivered. As yet another alternative, the programmer may be employed to simply abort the therapy during the warning delay, which may be especially useful if therapy was initially requested by the patient, and the patient's symptoms have subsided.

A warning system as described above, including apparatus specifically dedicated to providing the warning may not be necessary if the patient can independently feel the analgesic take effect.

Figure 5:
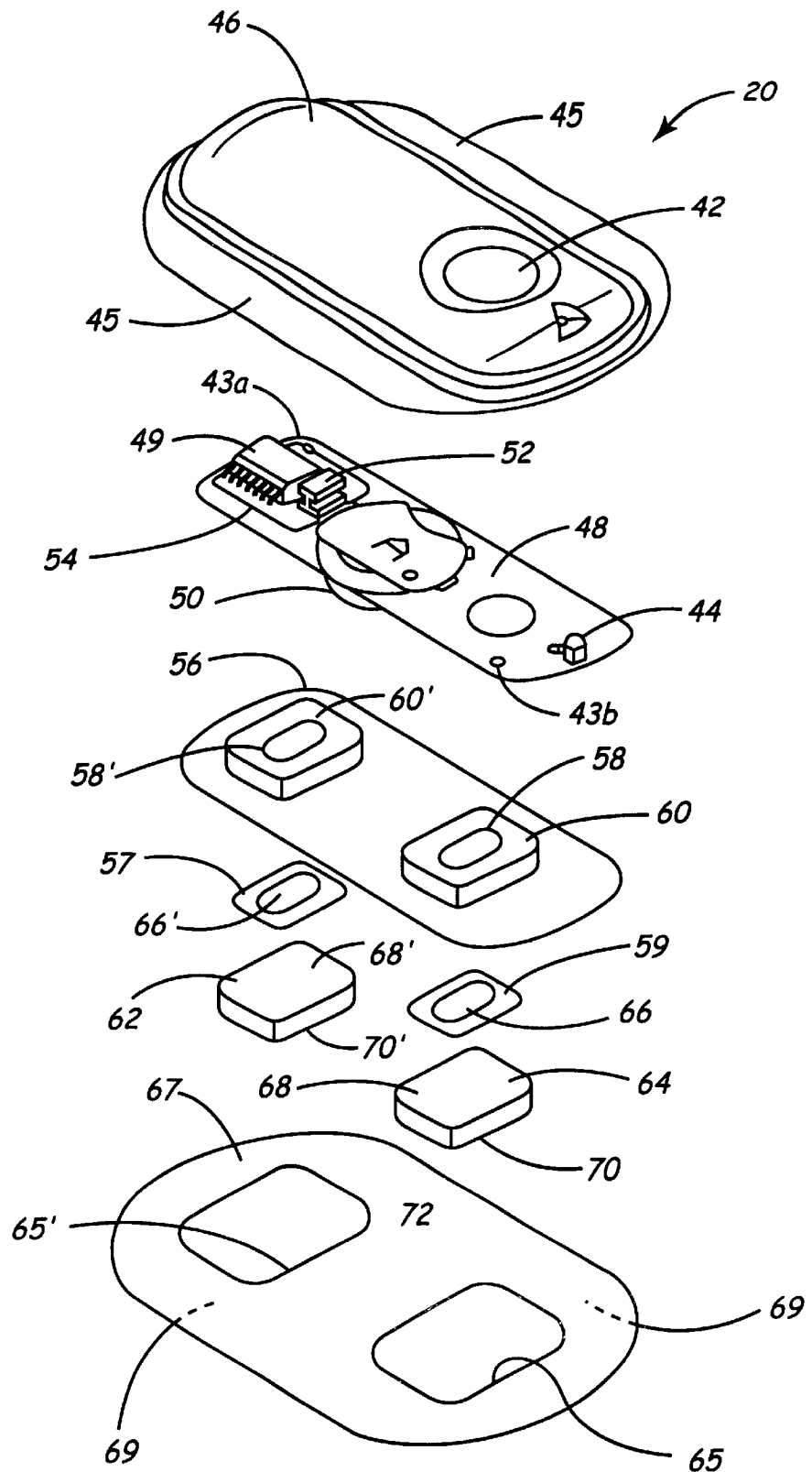
FIG. 5 illustrates a representative drug delivery device.

FIG. 5 illustrates a representative electrotransport delivery device that may be used in conjunction with the present invention. Device 20 comprises an upper housing 46, a circuit board assembly 48, a lower housing 56, anode electrode 57, cathode electrode 59, anode reservoir 62, cathode reservoir 64 and skin-compatible adhesive 67. Upper housing 46 has lateral wings 45, which assist in holding device 20 on a patient's skin. Upper housing 46 is preferably composed of an injection moldable elastomer (e.g., ethylene vinyl acetate). Printed circuit board assembly 48 comprises an integrated circuit 49 coupled to discrete components 52, antenna 54 and battery 50. Circuit board assembly 48 is attached to housing 46 by posts (not shown in FIG. 5) passing through openings 43a and 43b, the ends of the posts being heated/melted in order to heat stake the circuit board assembly 48 to the housing 46. Lower housing 56 is attached to the upper housing 46 by means of adhesive 67, the upper surface 72 of adhesive 67 beings adhered to both lower housing 56 and upper housing 46 including the bottom surfaces of wings 45.

Shown (partially) on the underside of circuit board assembly 48 is a button cell battery 50. Other types of batteries may also be employed to power device 20.

The device 20 is generally comprised of battery 50, electronic circuitry 49, 52, 54, electrodes 57, 59, and hydrogel drug reservoirs 62, 64, all of which are integrated into a self-contained unit. The outputs (not shown in FIG. 5) of the circuit board assembly 48 make electrical contact with the electrodes 59, and 57 through openings 58, 58' in the depressions 60, 60' formed in lower housing 56, by means of electrically conductive adhesive strips 66, 66'. Electrodes 57 and 59, in turn, are in direct mechanical and electrical contact with the top sides 68, 68' of drug reservoirs 62 and 64. The bottom sides 70', 70 of drug reservoirs 62, 64 contact the patient's skin through the openings 65', 65 in adhesive 67.

Device 20 optionally has a feature, which allows the patient to self-administer a dose of drug by electrotransport. Upon depression of push button switch 42, the electronic circuitry on circuit board assembly 48 delivers a predetermined DC current to the electrode/reservoirs 57, 62 and 59, 64 for a delivery interval of predetermined length. The push button switch 42 is conveniently located on the top side of device 20 and is easily actuated through clothing. A double press of the push button switch 42 within a short time period, e.g., three seconds, is preferably used to activate the device for delivery of drug, thereby minimizing the likelihood of inadvertent activation of the device 20. Preferably, the device transmits to the user a visual, tactile and/or audible confirmation of the onset of the drug delivery interval by means of LED 44 becoming lit, TENs-like stimulation via electrodes 57 and 59 and/or an audible sound signal from, e.g., a "beeper". Drug is delivered through the patient's skin by electrotransport, e.g., on the arm or body, over the predetermined delivery interval.

Anodic electrode 57 is preferably comprised of silver and cathodic electrode 59 is preferably comprised of silver chloride. Both reservoirs 62 and 64 are preferably comprised of polymeric gel materials. Electrodes 57, 59 and reservoirs 62, 64 are retained by lower housing 56.

A liquid drug solution or suspension is contained in at least one of the reservoirs 62 and 64. Drug concentrations in the range of approximately $1 \times 10^{-4}$ M to 1.0 M or more can be used, with drug concentrations, in the lower portion of the range being preferred. Typically, the reservoir containing the drug will also contain the selected countersensitizing agent, in an amount and concentration effective to provide the flux necessary to reduce or prevent sensitization of the skin or mucosa.

Figure 6:
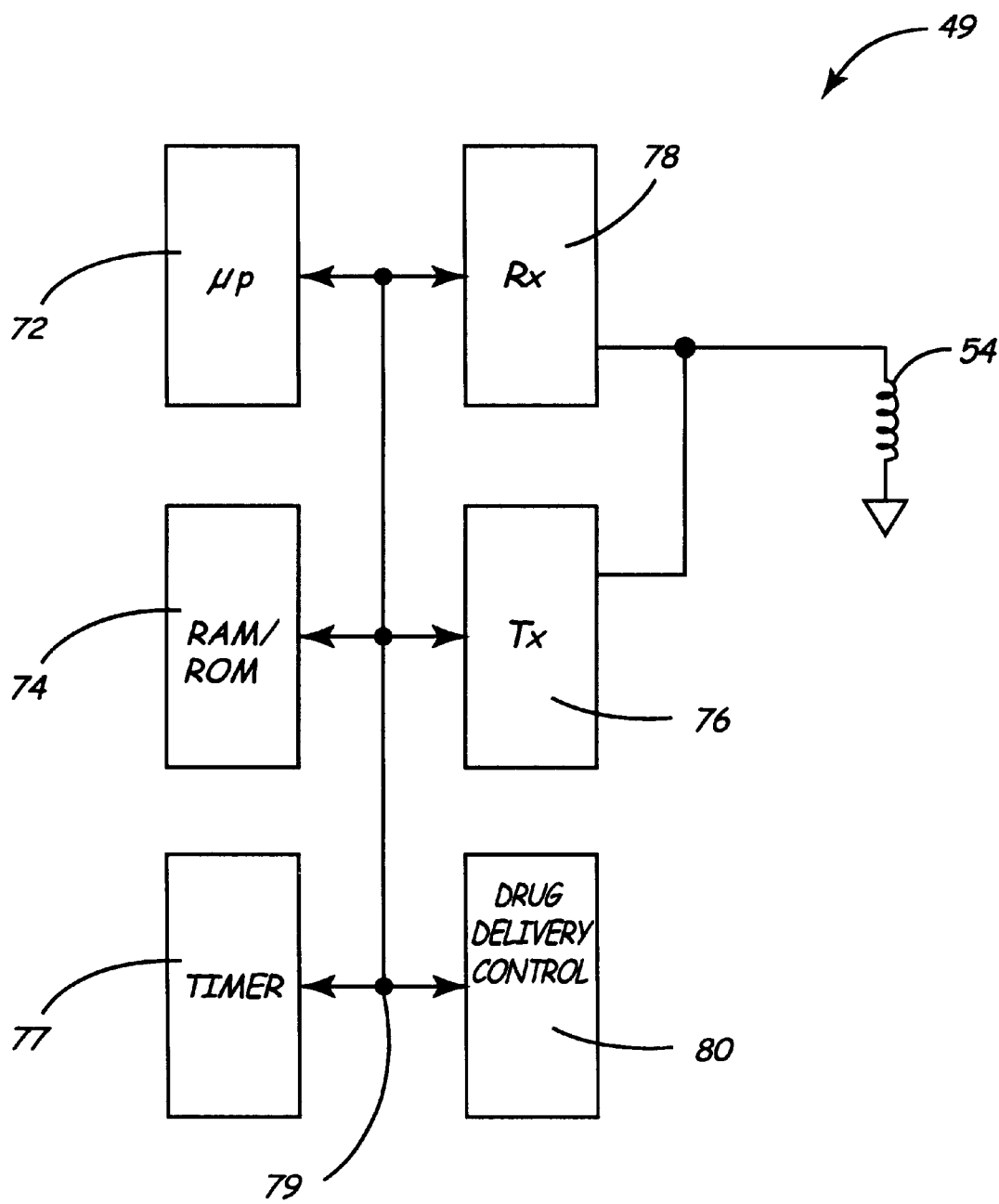
FIG. 6 depicts a drug delivery system schematic block diagram.

FIG. 6 shows a simplified schematic block diagram of drug delivery system 20 integrated circuit 49. Microprocessor 72 under control of a program contained in RAM/ROM 74 (interconnected via bidirectional bus 79) receives commands from IMD 12 through receiver 78 and antenna 54. Upon a command to initiate drug delivery, the microprocessor 72 initiates drug delivery through drug delivery control block 80, which initiates iontophoretic drug delivery through two electrodes (not shown). Timer 77 times the length of time for drug delivery under control of intervals stored in RAM/ROM 74 previously programmed via programmer 22 (not shown in FIG. 6). Upon timer 77 time out, a signal is sent to IMD 12 from transmitter block 76 and antenna 54 using the same telemetry system described herein above.

The infusion of various analgesic drugs or agents (or, simply "analgesics") including opiates (i.e. morphine sulfate, hydromorphone) and non-opiates (i.e. alpha-2 adrenergic agonists and neuron specific calcium channel blocking agents) have demonstrated rapid and effective analgesia following administration. Dependent upon the specific analgesic administered, it is also reported that the onset of pain suppression occurs in a couple of minutes to one hour, and the duration of analgesia may range from 4–24 hours. The delay in analgesia onset is not problematic, since rapid cardioversion is not necessary for atrial fibrillation as opposed to ventricular fibrillation. Time to analgesia can be utilized by the system 30 to re-verify the continuation of atrial fibrillation, charge storage capacitors to deliver the cardioversion shock, and ensure ventricular sensing to allow cardioversion shock synchronization with the R-wave of the cardiac cycle.

A first alternative embodiment of the invention may employ the drug delivery system 20 for delivery of a cardioversion or defibrillation threshold reducing agent such as D-salotol, Procainamide or Quinidine as an alternative to, or in conjunction with, delivery of the pain alleviating therapy discussed above. The reduction of defibrillation threshold in such case would provide the possibility of a reduced amplitude, less painful cardioversion pulse. The delivery of a threshold reducing agent thus can be employed as a pain alleviating therapy or as part of a pain alleviating therapy. In a more complex embodiment, two separate drug delivery systems might be employed to allow delivery of the threshold reducing agent alone or in conjunction with an analgesic.

A second alternative embodiment of the invention may employ the drug delivery system 20 for delivery of diuretic and blood pressure regulating agents such as Thiazide diuretics (hydrochlorothiazide, chlorthalidone), usually adequate for mild heart failure, loop diuretics (furosemide, bumetanide, ethacrynic acid) reserved for severe volume overload or thiazide-resistant edema. Additionally, ACE inhibitors have been shown to prevent or slow the progression of heart failure in patients with symptomatic and asymptomatic left ventricular dysfunction. Currently, four agents are used for the treatment of CHF (Congestive Heart Failure): captopril, enalapril, lisinopril, and quinapril. The implementation of IMD 12 of this embodiment would use the Medtronic Chronicle™ CHF monitoring system such as described in U.S. Pat. Nos. 5,535,752 and 6,155,267, incorporated herein by reference in their entireties. The IMD 12, as described in the '267 patent, would monitor chronic data representative of at least one physiological parameter. The chronic data is monitored to detect changes in state of the at least one physiological parameter. Data associated with detected changes in state is stored within IMD 12. The detection of changes in state of the at least one physiological parameter is performed by establishing a baseline (e.g., a center reference line and upper and lower control limits), and then determining if the chronic data being monitored satisfies predetermined, preprogrammed conditions (e.g., conditions based on the center reference line and the upper and lower control limits) indicative of a change in state of the at least one physiological parameter. If data occurs outside of these predetermined limits, the IMD 12 sends telemetry signals to drug delivery system 20 to initiate the delivery of the appropriate drug as described herein above.

A third alternative embodiment may utilize the drug delivery system 20 as the patient activator/programmer 22 by incorporating the features and function as described in U.S. Pat. No. 5,987,356 incorporated herein by reference in its entirety.

Figure 7:
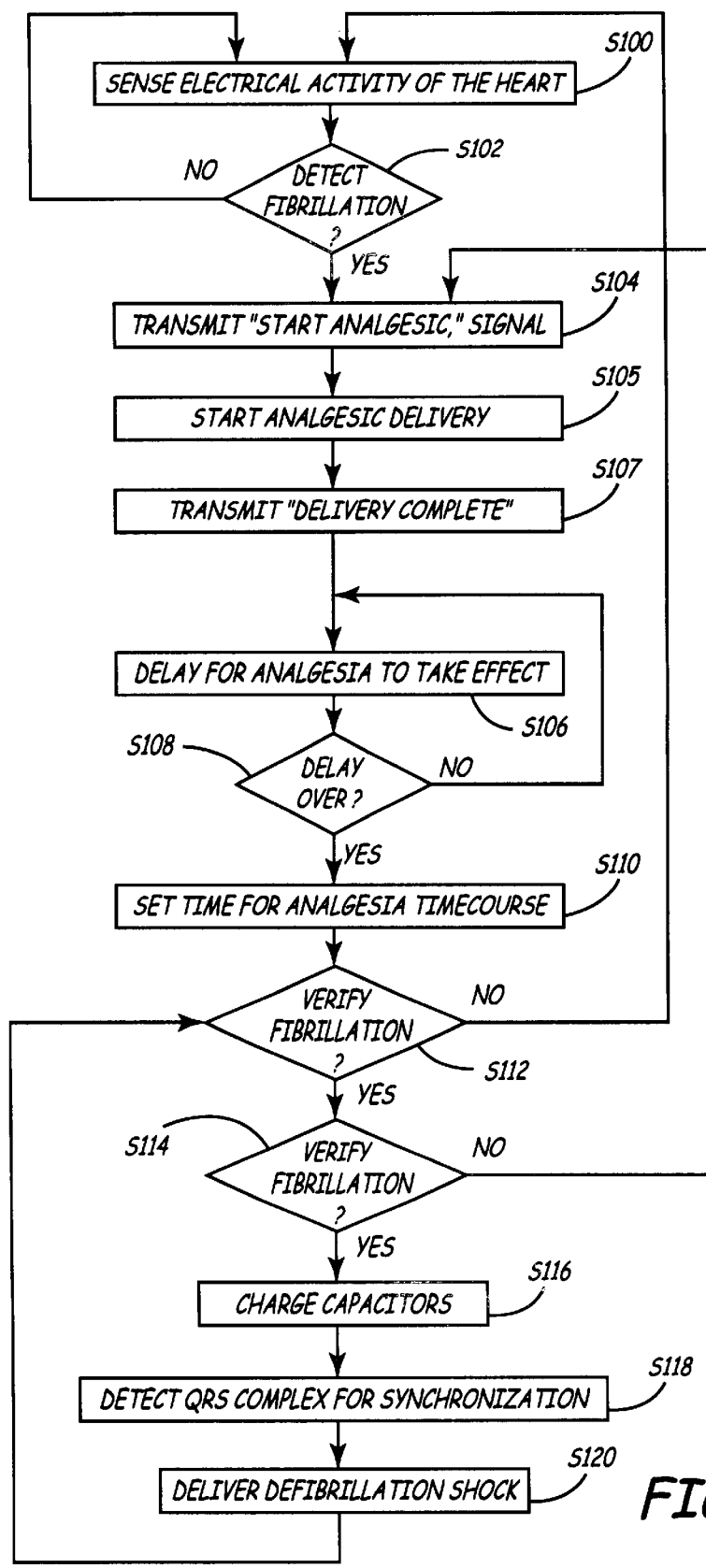
FIG. 7 represents a high-level logic flow diagram of the present invention.

FIG. 7 depicts a flow chart of an operation of the system shown in FIG. 4 in accordance with the present invention. At step S100, which continues at all times (except during the delivery of atrial cardioversion shock), atrial activity of the heart is sensed. At step 102, the atrial fibrillation detection algorithm is invoked in atrial fibrillation detector 270. If it is detected, then in step S104, the IMD 30 transmits a signal to the drug delivery system 20 via drug delivery control 290, RF transmitter 292 and antenna 294 to initiate delivery at S105 of a programmed bolus of the pain alleviating drug from drug dispenser 20.

The charge delivery control 272 may be commanded to start charge up of the charge storage capacitors, but it is preferred to delay capacitor charge up until the end of the delay for the analgesic to take effect and commence capacitor charge up during the analgesic time course, that is, the time period that the analgesia effect is expected to continue. At S107 the drug delivery device 20 transmits a confirmation of drug delivery completion back to the IMD 12. Optional warning steps for the patients to show the status of the detection, drug delivery and cardioverter status may be included but are not shown in the flow chart of FIG. 7.

A delay timer 265 is loaded and enabled to time out the delay for the analgesia effect to take place in steps S106 and S108. During this delay, the continuation of the atrial fibrillation episode may be verified in steps S100 and S102 and the algorithm may optionally be halted at that point. However, since atrial fibrillation bouts reoccur and since the bolus of pain alleviating drug is already delivered, re-confirmation at the end of the delay times is sufficient to determine whether or not to deliver the cardioversion shock therapy.

When the delay timer 265 times out in step S108, the delay timer 265 is reset for the analgesic time course and is started in step S110. The atrial fibrillation detection is re-verified in step S112 during the analgesic time course. If it only re-verified after the analgesic time course times out, then it is necessary to repeat steps S104–S114 until it is re-verified during an analgesic time course.

Then, in step S116, a charge delivery control 272 is commanded to enable the storage capacitor charge circuit 274 to charge the high voltage output capacitors up to the cardioversion energy set in level stage 269. The microcomputer 262 then sets a synchronization time interval in interval set stage 266 from an R-wave detected by R-wave detector 252. The ventricular timer 264 then provides a blanking signal to the ventricular and atrial sense amplifiers 250 and 254. Both operations may be performed in step S118. Re-verification of continued atrial fibrillation may also be performed between steps S116 and S118.

At the expiration of the synchronization time interval in ventricular timer 264, a command is applied through the charge delivery control to operate a discharge circuit 276 to discharge the atrial cardioversion shock via electrodes 244 and 246. After the atrial cardioversion shock is delivered, the atrial and ventricular sense amplifiers are again enabled, and the presence or absence of atrial fibrillation is again tested in step S112. If the episode is terminated, then the algorithm loops back to step S100.

If the episode is not terminated, the steps of FIG. 7 may be repeated. After a certain number of attempts, the available therapies may be exhausted. Whether or not the therapies are successful, the patient will likely have been advised to contact the attending physician. The event history of the episodes and delivered therapies are recorded in RAM 282 for subsequent telemetry out and analysis by the physician in a manner well known in the art in order to assist in reprogramming therapies.

Thus, the methodological sequence to provide the pain alleviating therapy to counter the pain induced by delivery of atrial cardioversion energy includes the initial detection of atrial fibrillation, optional warning to the patient, drug infusion therapy to produce analgesia, time out to allow analgesia to take effect and the charge storage capacitors to be charged, reverification of atrial fibrillation, delivery of the cardioversion energy, and verification that successful atrial defibrillation has taken place. Should successful atrial cardioversion not take place, the steps of FIG. 7, would be reinitiated, except that analgesic drug delivery would not be repeated unless the analgesic time course time had timed out in order to prevent drug overdose.

Depending on the analgesic employed, it may also be desirable to include a further timer to inhibit delivery of a further analgesic bolus timed from the previous delivery for a further time delay to prevent drug overdose. Such a timer may take into account the cumulative amount of analgesic delivered over a set time period.

In addition, it may be desireable to provide the patient with the option of using programmer 22 to temporarily program the delivery of an increased quantity of analgesic, if the desired analgesia effect is not achieved at the permanently programmed setting. A time and date record of such patient programmed increases may be kept in the system memory for review by the physician, and the repetitive use of the programmer may be inhibited.

The preceding specific embodiments are illustrative of the practice of the invention. It is to be understood, therefore, that other expedients known to those of skill in the art or disclosed herein may be employed without reporting from the invention or the scope of the appended claim. It is therefore to be understood within the scope of the appended claims; the invention may be practiced otherwise than is specifically described, without departing from the scope of the present invention.

What is claimed is:

1. A drug delivery strip in communication with an implantable medical device (IMD), the combination comprising:
   means for monitoring at least one pretherapy event in the IMD;
   means for communicating to the drug delivery strip that said at least one pretherapy event is imminent; and
   means for activating the delivery of drugs from the drug delivery strip prior to or contemporaneous with a therapy resulting from said at least one pretherapy event.

2. The combination of claim 1 wherein said therapy event includes the delivery of cardioversion/defibrillation energy.

3. The combination of claim 1 wherein said therapy event includes the delivery of energy shock to the heart.

4. A transdermal drug delivery device in wireless communications with at least one implantable medical device (IMD) wherein the drug delivery device is adapted to be externally mounted to a patient to deliver pain analgesics and/or threshold reduction medications prior to a shock associated with a pacer, a defibrillator and similar therapy device, the drug delivery device comprising:
   means for storing the medications;
   means for mounting epidermally to a patient;
   means for communicating with at least one IMD; and
   means for releasing the medications transdermally responsive to at least one indication that the at least one IMD is about to deliver the shock.

5. A transdermal drug delivery device in combination with an implantable medical device (IMD) to deliver medications to a CHF patient, the combination comprising:
   the drug delivery device adapted to be externally mounted on a patient;
   the IMD being a CHF monitoring device; and
   a communication system between the drug delivery device and the IMD to enable the delivery of the medications prior to or contemporaneous with CHF signals from the IMD.

6. The combination of claim 5 wherein said signals include parameters that lie outside a pre-selected range of cardiac events.

7. An external drug delivery device adapted to be mounted to the skin of a patient and in communication with an IMD to deliver specialty drugs responsive to signals from the IMD relating to cardiac conditions and/or therapy, the drug delivery device having storage for the specialty drugs, the drugs comprising:
   opiates;
   non-opiates;
   defibrillation threshold reducing agents; and
   agents for treatment of CHF.

8. The drug delivery device of claim 7 wherein said opiates include morphine sulfate and hydromorphine.

9. The drug delivery device of claim 7 wherein said non-opiates include alpha-2 adreneorgic agonists and neuron specific calcium channel blocking agents.

10. The drug delivery device of claim 7 wherein said defibrillation threshold reducing agents include D-salotol, Procainamade or Quinidine as alternatives or in combination with one or both said opiates and said non-opiates.

11. The drug delivery device of claim 7 wherein said agents for treatment of CHF includes captopril, enalapril, lisinopril and quinapril.

12. The drug delivery device of claim 7 wherein said specialty drugs include drugs designed to overcome pain and threshold associated with cardiac shock.

13. The drug delivery device of claim 7 wherein said specialty drugs include drug types designed to treat CHF conditions.

14. The drug delivery device of claim 13 wherein the drug types are suited to treat pain, threshold, and CHF conditions in combination thereof.

15. An external drug delivery device in communication with an implantable medical device (IMD) forming a system in which one or more drugs are discharged into a patient based on signals received from the IMD, the system comprising:
   a communication link between the drug delivery device and the IMD;
   automatic means for discharging the one or more drugs from the external drug delivery device into the patient when the signals are received from the IMD via said communication link; and
   automatic means for terminating the discharge of the one or more drugs.

16. The system of claim 15 wherein a semi-automatic means for discharging is implemented to enable the patient to activate the drug discharge on an as-needed basis.

17. The system of claim 15 wherein a semi-automatic means for terminating the discharge is implemented to enable the patient to terminate the drug discharge on as needed basis.

18. The system of claim 15 wherein the communication link includes system status indicators.

19. The system of claim 15 wherein said system status indicators include visual displays.

20. The system of claim 15 wherein said system status indicators include audible signals.

21. The system of claim 15 wherein said system status indicators include tactile interfaces.

22. The system of claim 15 wherein the communication link includes override means to enable the patient to terminate or delay shock using the drug delivery device as a controller.

23. The system of claim 15 wherein the communication link includes remote monitoring and programing means to enable remote patient management.

24. A system for delivering cardioversion energy to at least one chamber of a patient's heart in need of cardioversion and for aleviating pain attendant to delivery of cardioversion energy comprising:
   a transdermal drug delivery device adapted to be applied to the patient's body responsive to a drug delivery command for transdermally delivering a drug into the patient's body when the chamber is determined to be in need of cardioversion, the drug comprising one or both of a cardioversion threshold reducing medication to reduce the cardioversion threshold and a pain alleviating medication to alleviate pain felt by the patient arising from the delivery of the cardioversion energy; and
   an implantable cardioversion/defibrillation device adapted to be implanted in the patient's body comprising:
      detecting means for detecting activity of a chamber of the patient's heart;
      determining means responsive to the detecting means for determining when the chamber of the patient's heart is in need of cardioversion;
      means responsive to the detecting means for transmitting the drug delivery command to the transdermal drug delivery device when the chamber of the patient's heart is in need of cardioversion; and
      cardioverting means responsive to the determining means for delivering cardioversion energy to the chamber of the patient's heart when the chamber is in need of cardioversion.

25. The system of claim 24 further comprising means for delaying delivery of the cardioversion energy by said cardioverting means from the delivery of the drug for a delay period sufficient to allow the drug to take effect.

26. The system of claim 25 wherein the means for delaying comprises means for timing out a delay period to allow the drug to take effect and further comprising:
   means operale upon time-out of the delay period for timing out a time course during which the drug remains effective;
   means responsive to the detecting means for determining whether the patient's heart chamber continues to be in need of cardioversion at any time during the time course; and
   means responsive to a determination that the patient's heart activity indicates a need for cardioversion during the time course for triggering delivery of the cardioversion energy to the heart chamber.

27. The system of claim 24 further comprising means responsive to the determining means for generating a patient warning of the imminence of the delivery of the cardioversion energy.

28. A method of delivering cardioversion energy to at least one chamber of a patient's heart in need of cardioversion comprising the steps of:
   detecting activity of a chamber of the patient's heart;
   determining when the chamber of the patient's heart is in need of cardioversion from the detected activity;
   transdermally delivering a bolus of a drug into the patient's body when the chamber is determined to be in need of cardioversion, the drug comprising one or both of a cardioversion threshold reducing medication to reduce the cardioversion threshold and a pain alleviating medication to alleviate pain felt by the patient arising from the delivery of the cardioversion energy; and
   delivering cardioversion energy to the chamber of the patient's heart when the chamber is determined to be in need of cardioversion.

29. The method of claim 28 further comprising delaying delivery of the cardioversion energy for a delay period sufficient to allow the drug to take effect.

30. The method of claim 29, wherein the step of delaying comprises timing out the delay period and further comprising:
   at the time-out of the delay period, timing out a time course during which the drug remains effective;

determining whether the patient's heart chamber continues to be in need of cardioversion during a time course of effectiveness of the drug following time-out of the delay period; and triggering delivery of the cardioversion energy during the time course following the time-out of the delay period in response to a determination that the patient's heart activity indicates a need for cardioversion of the heart chamber during the time course.

31. The method of claim 28 further comprising the step of generating a patient warning of the imminence of the delivery of the cardioversion energy.

32. A method of delivering cardioversion energy to at least one chamber of a patient's heart in need of cardioversion comprising the steps of:

detecting activity of the at least one chamber of the patient's heart;

determining from the detected activity when the at least one chamber of the patient's heart is in need of cardioversion;

upon determining the need for cardioversion, transdermally delivering a drug into the patient's body, the drug comprising one or both of a cardioversion threshold reducing medication to reduce the cardioversion threshold and a pain alleviating medication to alleviate pain in body tissue arising from the delivery of the cardioversion energy;

timing out a delay period from the determination of the need for cardioversion sufficient for the applied drug to take effect; and delivering cardioversion energy to the at least one chamber of the patient's heart following time-out of the delay period and during a time course of effectiveness of the delivered drug.

33. The method of claim 32, wherein the cardioversion delivering step further comprises:

determining whether the patient's heart chamber continues to be in need of cardioversion during the time course of effectiveness of the delivered drug; and initiating delivery of the cardioversion energy during the time course of effectiveness of the delivered drug only in response to a determination that the patient's heart activity indicates a need for cardioversion of the heart chamber.

34. A system for delivering cardioversion energy to at least one chamber of a patient's heart in need of cardioversion comprising:

means for detecting activity of the at least one chamber of the patient's heart;

means for determining from the detected activity when the at least one chamber of the patient's heart is in need of cardioversion;

transdermal drug delivery means operable upon determining the need for cardioversion for transdermally delivering a drug into the patient's body, the drug comprising one or both of a cardioversion threshold reducing medication to reduce the cardioversion threshold and a pain alleviating medication to alleviate pain in body tissue arising from the delivery of the cardioversion energy;

means for timing out a delay period from the determination of the need for cardioversion sufficient for the applied drug to take effect; and means for delivering cardioversion energy to the at least one chamber of the patient's heart following time-out of the delay period and during a time course of effectiveness of the delivered drug.

35. The system of claim 34, wherein the cardioversion delivering means further comprises means for initiating delivery of the cardioversion energy during the time course of effectiveness of the delivered drug only in response to a determination by the determining means that the patient's heart activity indicates a need for cardioversion of the heart chamber during the time course.

36. An atrial cardioversion system, comprising an implantable cardioverter adapted to be implanted in the patient's body, an external drug delivery device adapted to attached to the patient's body, and a patient operated external programmer for communication with the implantable cardioverter and the external drug delivery device wherein:

the external programmer comprises means operable by the patient for transmitting a patient activated command signal to initiate delivery of a drug and a cardioversion therapy when the patient experiences symptoms of atrial fibrillation;

the external drug delivery device comprises means responsive to the command signal transmitted from the external programmer for transdermally delivering a bolus of a drug into the patient's body, the drug comprising one or both of a cardioversion threshold reducing medication to reduce the cardioversion threshold or a pain alleviating medication to alleviate pain felt by the patient arising from the delivery of the cardioversion energy;

the implantable cardioverter comprises:

means for receiving the command signal transmitted from the external programmer;

delaying means responsive to the command signal for timing a delay period sufficient for the delivered drug to take effect; and cardioversion energy generator means for delivering atrial cardioversion energy to the patient's atria upon time-out of the delay period in response to the command signal.

37. The system of claim 36 wherein the implantable cardioverter further comprises:

means operable upon time-out of the delay period for timing out a time course during which the drug remains effective;

detecting means for determining whether the patient's atria continue to be in need of cardioversion at any time during the time course; and cardioversion energy trigger means responsive to a determination that the patient's heart activity indicates a need for cardioversion during the time course for triggering delivery of the cardioversion energy to the atria.

38. The system of claim 37 wherein the implantable cardioverter further comprises:

means for detecting a ventricular depolarization of the patient's heart; and the cardioversion energy trigger means triggers delivery of the cardioversion energy to the atria in timed relation to the detected ventricular depolarization.

39. The system of claim 36 wherein the implantable cardioverter further comprises means responsive to the determining means for generating a patient warning of the imminence of the delivery of the cardioversion energy.

40. A method of operating an atrial cardioversion system, comprising an implantable cardioverter adapted to be implanted in the patient's body, an external drug delivery device adapted to attached to the patient's body, and a patient operated external programmer that the patient employs to transmit a patient activated command signal to initiate delivery of a drug and a cardioversion therapy when the patient experiences symptoms of atrial fibrillation, comprising:

transdermally delivering a bolus of a drug into the patient's body in response to the command signal transmitted from the external programmer, the drug comprising one or both of a cardioversion threshold reducing medication to reduce the cardioversion threshold or a pain alleviating medication to alleviate pain felt by the patient arising from the delivery of the cardioversion energy; and within the implantable cardioverter,
receiving the command signal transmitted from the external programmer;
in response to the command signal, timing a delay period sufficient for the delivered drug to take effect; and
delivering atrial cardioversion energy to the patient's atria upon time-out of the delay period.

41. The method of claim 40, further comprising the steps of the implantable cardioverter of:
upon time-out of the delay period, timing out a time course during which the drug remains effective;
determining whether the patient's atria continue to be in need of cardioversion at any time during the time course; and
triggering delivery of the cardioversion energy to the atria only in response to a determination that the patient's heart activity indicates a need for cardioversion of the atria during the time course.

42. The method of claim 40 further comprising the steps of the implantable cardioverter of:
upon time-out of the delay period, timing out a time course during which the drug remains effective;
determining whether the patient's atria continue to be in need of cardioversion at any time during the time course;
detecting a ventricular depolarization of the patient's heart; and
triggering delivery of the cardioversion energy to the atria in timed relation to the detected ventricular depolarization only in response to a determination that the patient's heart activity indicates a need for cardioversion of the atria during the time course.

43. The method of claim 40 further comprising the step of the implantable cardioverter of generating a patient warning of the imminence of the delivery of the cardioversion energy.

44. An atrial cardioversion system, comprising an implantable cardioverter adapted to be implanted in the patient's body, an external drug delivery device adapted to attached to the patient's body, and a patient operated external programmer for communication with the implantable cardioverter wherein:

the external programmer comprises means operable by the patient for transmitting a patient activated command signal to initiate delivery of a cardioversion therapy when the patient experiences symptoms of atrial fibrillation;

the implantable cardioverter comprises:
means for receiving a request of the patient activated command signal;
means for timing a delay period; and
cardioversion energy generator means for delivering a cardioversion energy to the patient's atria upon time-out of the delay period; and the external drug delivery device comprises means responsive to a command from one of the patient, the external programmer or the implantable cardioverter for transdermally delivering one or both that takes effect during the timing out of the delay period.

45. The system of claim 44 wherein the implantable cardioverter further comprises:
means for determining whether the patient's heart activity continues to indicate a need for atrial fibrillation substantially on time-out of the delay period; and
means responsive to a determination that the patient's heart activity does not indicate a need for a trial fibrillation for inhibiting delivery of atrial cardioversion energy.

46. The system of claim 44 wherein the implantable cardioverter includes means for restarting the delay period in response to a request of the patient transmitted by the external programmer for delaying atrial cardioversion.

\* \* \* \* \*